United States Patent
Nuernberger et al.

(10) Patent No.: US 8,394,046 B2
(45) Date of Patent: Mar. 12, 2013

(54) METHOD AND DEVICE FOR CHECKING THE CORRECT COUPLING OF A SUPPLY DEVICE TO A THERAPY DEVICE

(75) Inventors: Thomas Nuernberger, Burkardroth (DE); Marco Blasek, Bad Kissingen (DE); Peter Kloeffel, Nuedlingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 559 days.

(21) Appl. No.: 12/451,565

(22) PCT Filed: May 13, 2008

(86) PCT No.: PCT/EP2008/003835
§ 371 (c)(1), (2), (4) Date: Nov. 19, 2009

(87) PCT Pub. No.: WO2008/145256
PCT Pub. Date: Dec. 4, 2008

(65) Prior Publication Data
US 2010/0130905 A1 May 27, 2010

(30) Foreign Application Priority Data
May 25, 2007 (DE) .......................... 10 2007 024 463

(51) Int. Cl.
*G01M 3/04* (2006.01)
*B01D 61/28* (2006.01)
*A61M 39/00* (2006.01)

(52) U.S. Cl. ..................... 604/5.01; 73/40.5 R; 73/49.8; 210/90; 210/321.6; 210/646; 210/741; 604/19; 604/27; 604/28; 604/65

(58) Field of Classification Search ............... 73/40.5 R, 73/46, 49.8, 865.9; 210/90, 97, 143, 258, 210/321.6, 321.71, 645–647, 739; 285/15, 285/93, 425; 604/4.01, 5.01, 6.09, 19, 27, 604/28, 30, 65–67, 151
See application file for complete search history.

(56) References Cited

U.S. PATENT DOCUMENTS

| 4,846,792 A | 7/1989 | Bobo, Jr. et al. |
|---|---|---|
| 5,015,226 A | 5/1991 | Polaschegg |
| 5,788,099 A | 8/1998 | Treu et al. |
| 6,090,048 A | 7/2000 | Hertz et al. |
| 6,558,347 B1 | 5/2003 | Jhuboo et al. |
| 6,579,253 B1 * | 6/2003 | Burbank et al. ............. 604/5.01 |
| 7,758,547 B2 * | 7/2010 | Tonelli et al. ................ 604/131 |

(Continued)

FOREIGN PATENT DOCUMENTS

| DE | 38 37 298 C1 | 3/1990 |
|---|---|---|
| DE | 196 05 260 A1 | 11/1996 |

(Continued)

*Primary Examiner* — Joseph Drodge
(74) *Attorney, Agent, or Firm* — Jacobson Holman PLLC (57) ABSTRACT

A method provides for checking the correct coupling of an adding device to a therapeutic appliance that includes an extracorporeal circuit with which the adding device is connected such that a drug can be introduced into the extracorporeal circuit by the adding device during operation of the therapeutic appliance. The adding device is coupled to the extracorporeal circuit on the suction side of a pump disposed in the extracorporeal circuit, with a portion in the region of negative pressure of the extracorporeal circuit being in connection with a portion of the adding device that is closed with respect to the other parts of the extracorporeal circuit, and with the pressure in the closed portion being varied and measured.

24 Claims, 6 Drawing Sheets

U.S. PATENT DOCUMENTS

| | | | |
|---|---|---|---|
| 7,938,792 B2 * | 5/2011 | Roger et al. | 604/6.09 |
| 8,133,194 B2 * | 3/2012 | Szamosfalvi et al. | 604/6.07 |
| 2005/0065459 A1 | 3/2005 | Zhang et al. | |
| 2006/0254982 A1 * | 11/2006 | Kopperschmidt | 210/646 |
| 2007/0158249 A1 * | 7/2007 | Ash | 210/138 |
| 2010/0192686 A1 * | 8/2010 | Kamen et al. | 73/290 R |
| 2010/0204633 A1 * | 8/2010 | Kopperschmidt | 604/5.04 |

FOREIGN PATENT DOCUMENTS

| | | |
|---|---|---|
| EP | 1 348 458 A1 | 10/2003 |
| JP | 02-289259 | 11/1990 |
| JP | 2002-095741 | 4/2002 |
| JP | 2005-218709 | 8/2005 |

* cited by examiner

METHOD AND DEVICE FOR CHECKING THE CORRECT COUPLING OF A SUPPLY DEVICE TO A THERAPY DEVICE

CROSS-REFERENCE TO RELATED APPLICATION

This is a national stage of PCT/EP08/003835 filed May 13, 2008 and published in German, which has a priority of German no. 10 2007 024 463.2 filed May 25, 2007, hereby incorporated by reference.

BACKGROUND OF THE INVENTION

1. Field of Invention

This invention relates to a method for checking the correct coupling of an adding device to a therapeutic appliance, which includes an extracorporeal circuit with which the adding device is connected such that during operation of the therapeutic appliance a drug can be introduced into the extracorporeal circuit by means of the adding device, which preferably is coupled on the arterial side of an extracorporeal blood circuit upstream or downstream of the blood pump.

2. Description of the Prior Art

From DE 38 37 298 C1, there is known an extracorporeal blood circuit with a heparin syringe infusing into the region of negative pressure on the suction side of the blood pump disposed in the arterial conduit, wherein an arterial clamp or an arterial valve is provided on the arterial blood conduit upstream of the infusion point and a pressure measurement point is provided before the blood pump in downstream direction. Here, it is described in detail how a metered amount of heparin can be supplied during blood treatment.

From U.S. Pat. No. 6,558,347 B1, there is known a peristaltic infusion pump for infusing a drug into a patient. There is described an apparatus and a method for checking the correct operation of a finger pump or the correct positioning of the tube in the finger pump. By closing a valve on the pressure side of the pump, a closed tube volume is produced, which is put under excess pressure by specifically starting the pump against the closed valve. The pressure in the corresponding tube portion is measured.

In an adding device coupled to a therapeutic appliance, it is of decisive importance that coupling is effected correctly. In particular when coupling on the suction side of a pump disposed in the extracorporeal circuit, a number of risks and errors can occur. The following possible errors can occur:

The adding device does not operate properly, whereby the drug to be added is sucked in incorrectly (problem of the unintended bolus);

when a conduit is not connected tightly, microbubbles will occur during suction;

when using foreign models of the adding device, e.g. heparin syringes of foreign manufacturers, a necessary compensation of play is not created, so that the adding device does not operate properly.

SUMMARY OF THE INVENTION

Therefore, it is the object of the present invention to create a method and an apparatus for checking the correct coupling of an adding device to a therapeutic appliance.

In accordance with the invention, the aforementioned object first of all is solved by a method as described herein. In the method with the features described herein, a portion of the extracorporeal circuit in connection with a portion of the adding device is closed with respect to the other parts of the extracorporeal circuit. In this closed region, the pressure is varied and measured.

In principle, a portion in the region of negative pressure on the suction side of the blood pump together with a portion of the adding device can be closed with respect to the other part of the extracorporeal circuit, in accordance with the invention. Optionally, however, a portion in the region of excess pressure on the pressure side of the blood pump together with a portion of the adding device can also be closed with respect to the other parts of the extracorporeal circuit.

Advantageous aspects of the invention can be taken from the sub-claims following the main claim.

Accordingly, a predetermined sequence of pressure conditions in the regions of negative and excess pressure preferably can be applied and measured, and the measured pressure profile can be compared with a set-point profile.

Advantageously, the adding device is a syringe pump with a syringe inserted therein.

The pump in the extracorporeal circuit advantageously is an occluding pump, in particular a peristaltic pump.

Advantageously, the pump can be a roller pump or a finger pump.

The drug supplied from the adding device, i.e. advantageously from the syringe pump, is an anticoagulant and advantageously heparin. However, the drug supplied can also be some other medicament, e.g. an iron preparation for additional medical treatment.

The pressure can be measured via a pressure sensor connected with the extracorporeal circuit.

Advantageously, the tube portions of the arterial conduit of a set of blood tubes for a method of extracorporeal blood treatment are subjected to different pressure conditions.

The changes in pressure can be effected by specifying the translational movement of the piston of a syringe pump and/or the angle of rotation of a peristaltic pump, wherein the changes in pressure specified by the translation and/or the angle of rotation are compared with the set-point profile or the set point. On the other hand, the set points or set-point profiles for the pressures also can be specified advantageously, and the required translational movements of the piston of a syringe pump and/or the angles of rotation of a peristaltic pump can be measured and be compared with the specified set points or set-point profiles of the translational movements or angles of rotation.

The torque of the motor for driving the syringe pump and/or the peristaltic pump can also be detected via the motor current and be specified as a set point or set-point profile.

Furthermore, the process sequences can be controlled by means of a control device, whereby an automation of the pressure profile check is possible. Instead of this automation, a manual check is, however, also possible in accordance with the invention. The advantageously provided control device can be integrated in the control of a blood treatment machine. Particularly advantageously, the control device controlling the process sequences can be retrofitted to a blood treatment machine.

The object is also solved by a therapeutic appliance with the features described herein. Accordingly, a therapeutic appliance, preferably a dialysis machine, which is suitable for accommodating an extracorporeal circuit with an adding device for concentrates with a diluent, includes a control device, in which the control unit is configured such that it automatically checks the correct coupling of the adding device by means of a method as described herein.

Advantageously, the adding device can be a syringe pump with a syringe inserted therein.

Via a tubular conduit, the syringe pump can be connected to a tubular conduit of the therapeutic appliance in the region of negative pressure on the suction side of a pump or also on the pressure side of a pump.

The syringe can be filled with a concentrate, for instance with an anticoagulant or quite particularly advantageously with heparin.

The tube portion is a portion of the arterial conduit of the set of blood tubes for a method of extracorporeal blood treatment.

Quite particularly advantageously, the therapeutic appliance with the aforementioned features can be used in dialysis, hemodialysis, hemofiltration, hemodiafiltration, for blood purification by adsorption, in transfusion methods or in autotransfusion methods.

BRIEF DESCRIPTION OF THE DRAWINGS

Further features, details and advantages of the invention will be explained in detail with reference to an embodiment illustrated in the drawing, in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modification within the spirit and scope of the invention will become apparent to those skilled in the art from this detailed description.

Figure 1:
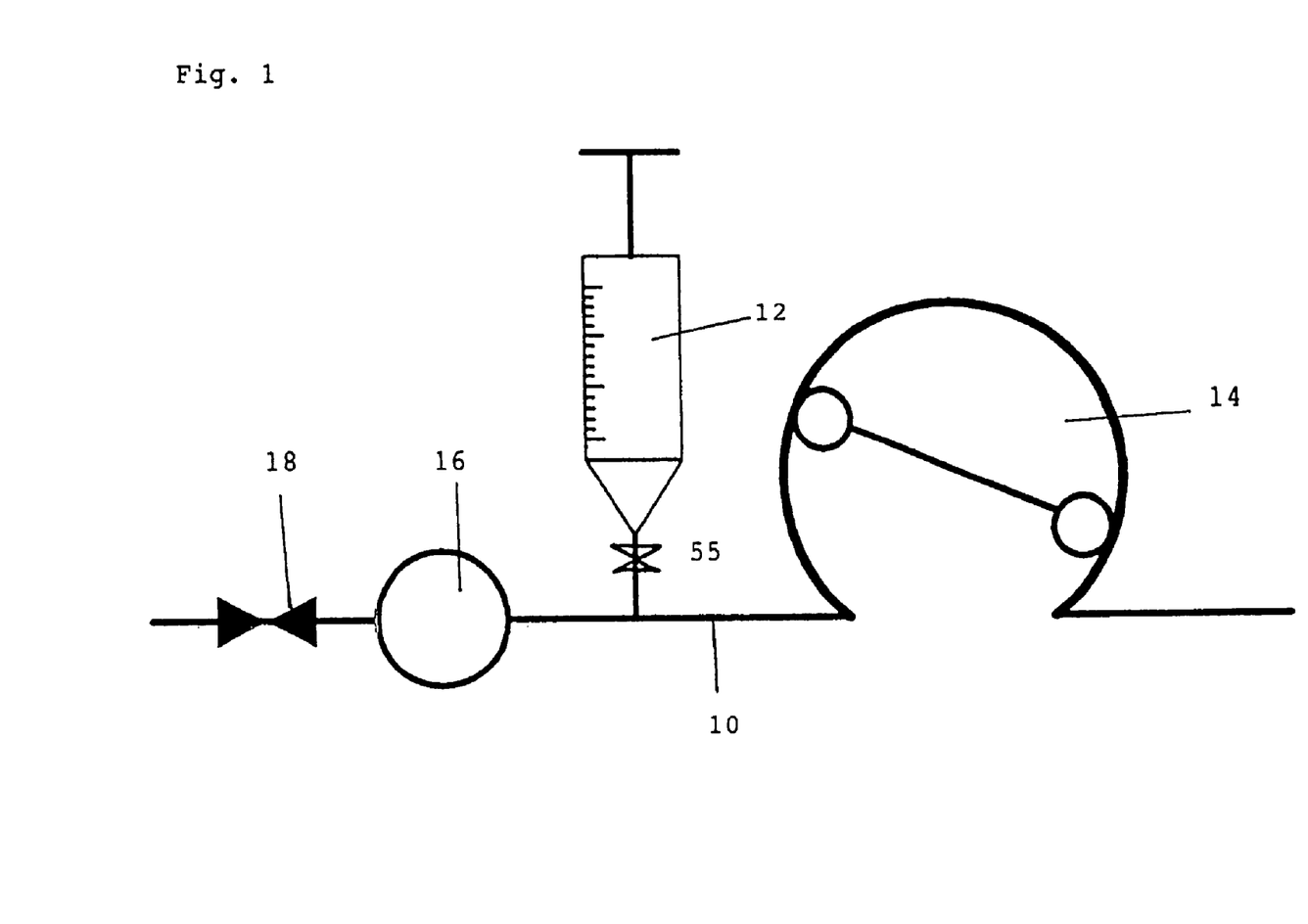
FIG. 1: shows a schematic representation of a part of a therapeutic appliance, in which the correct coupling of an adding device can be checked.

FIG. 1 schematically shows a portion of the arterial conduit 10 of the set of blood tubes for a method of extracorporeal blood treatment, to which a syringe 12 is connected. The syringe 12 is disposed in the region of negative pressure of a peristaltic pump 14, for instance an occluding roller pump 14. Furthermore, an arterial pressure measurement unit 16 is connected in the arterial conduit 10. Via an arterial clamp 18 and by the occlusion of the occluding roller pump 14 and the syringe 12 (also described herein as a "pump" or a "heparin pump"), the part of the arterial conduit illustrated here in FIG. 1 can be closed with respect to the surroundings. For checking the correct coupling of a syringe 12 in a non-illustrated syringe pump and for checking the tightness of the portion of the extracorporeal blood circuit 10 in the region of negative pressure on the suction side of the blood pump 14, the tube portion 10 is maintained closed by the arterial clamp 18, the syringe 12 and the occluding blood pump 14, the pressure in the closed tube portion 10 being changed and measured. By means of the blood pump 14 and the pump 12, a certain sequence of pressure conditions in the region of negative pressure and/or excess pressure is applied in the tube portion 10, the measured pressure profile being compared with a set-point profile. The syringe illustrated here can be a heparin syringe 12 prefilled with a concentrate, which after a corresponding check and upon confirmation of the tightness and proper operation is deliberately charged at the extracorporeal blood circuit and diluted such that the desired heparin concentration is produced, which is to be added later.

The sequence of pressure conditions applied for test purposes includes both excess pressures and negative pressures based on the starting pressure. The negative pressures can be generated in particular by reverse movement of the pump 12 and/or by forward movement of the roller pump 14. Similarly, excess pressures can be generated by forward movement of the syringe 12 and/or by reverse movement of the roller pump 14.

Figure 2:
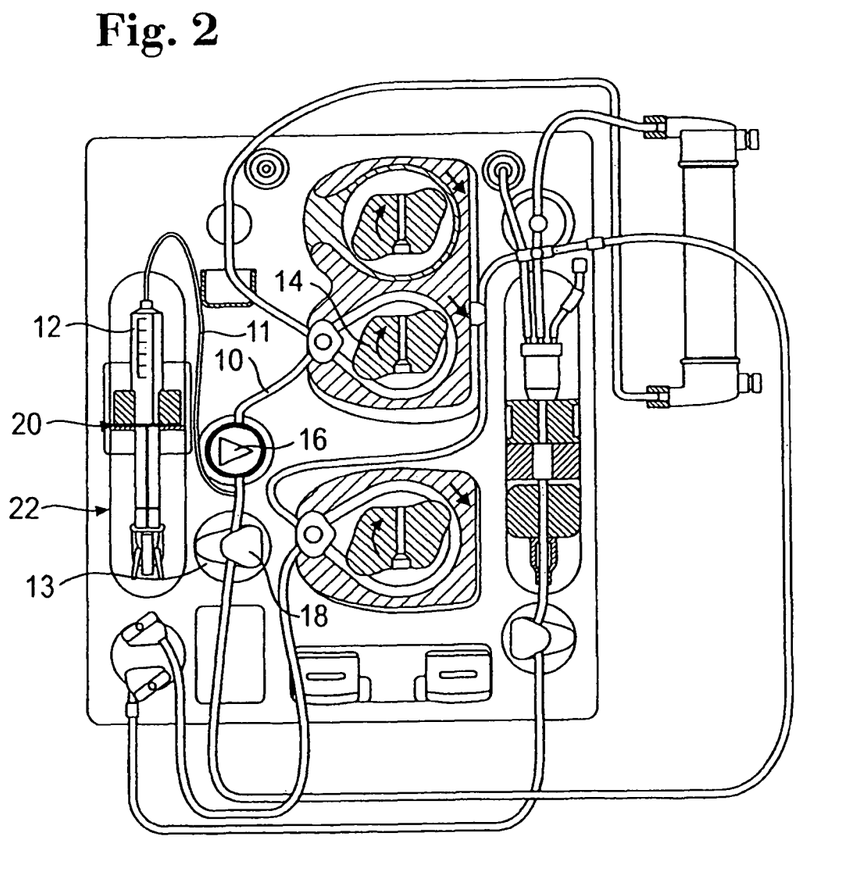
FIG. 2: shows one variant of an extracorporeal circuit.

FIG. 2 shows a concrete configuration of the region schematically illustrated in FIG. 1. Here, a syringe 12 is inserted in the vicinity of a syringe pump 13, wherein the wings 20 of the cylinder of the syringe 12 are fixed here and the plunger of the syringe piston is moved correspondingly. Via a tube 11, the syringe 12 is connected with the arterial tube portion 10. Reference numeral 14 designates the roller pump, by means of which the arterial blood can be delivered. The pressure sensor 16 and the arterial clamp 18 are automated in the apparatus as shown in FIG. 2. This is an extracorporeal blood circuit of a dialysis device.

Checking the correct coupling of the heparin pump, i.e. the syringe 12, is effected for instance as follows. The blood pump 14 rotates into the normal position, for instance with a delivery rate of 100 ml/min. Subsequently, the arterial clamp 18 is closed. The blood pump possibly decreases an arterial pressure to $\leq 0$ mmHg. This must be achieved within a specific angle of rotation of the pump. Otherwise, the heparin pump connection test has failed. When the arterial pressure has been decreased, the blood pump starting angle is stored. Subsequently, the blood pump generates a negative arterial pressure of $\leq -200$ mmHg. The same must be reached from the starting angle with a maximum rotation of the blood pump of 36°. Otherwise, the heparin pump connection test has failed. Then, one will wait for 5 seconds, so that the pressure can stabilize. Subsequently, the arterial starting pressure is stored. The heparin pump, i.e. the syringe 12, delivers forward, until the arterial pressure has increased by +50 mmHg with respect to the starting pressure. This must be achieved with a delivery volume of the heparin pump, i.e. the syringe 12, of maximally 2.0 ml. Otherwise, the heparin pump connection test has failed.

The heparin pump, i.e. the syringe 12, subsequently delivers backward, until the starting pressure is reached again. If the starting pressure was $\geq -50$ mmHg, backward delivery is continued, until the arterial pressure is $\leq -50$ mmHg. This must be achieved with a delivery volume of the heparin pump of maximally 2.0 ml. Otherwise, the connection test has failed.

After a passed or also a failed heparin pump connection test, the blood pump is stopped for 2 seconds and the clamps are opened, in order to effect a compensation of pressure.

For the case that the heparin pump connection test in preparing including circulating has not been performed or has failed, or if the user upgrades the heparin syringe 12 with a delay, a warning will be issued when proceeding to dialysis, informing the user that heparinization must be checked.

In principle, the aforementioned test can also be performed during treatment of a patient.

The following errors can be detected during the pressure test:

clamp 55 at the heparin conduit is closed;
heparin conduit 11 is bent;
heparin conduit 11 not connected to syringe;
syringe plunger 22 not engaged in handle piece; and
handle piece not coupled to drive (detent mechanism actuated).

With reference to FIGS. 3 to 6, different pressure profiles are shown, which reveal different cases of error and also the ideal case.

Figure 3:
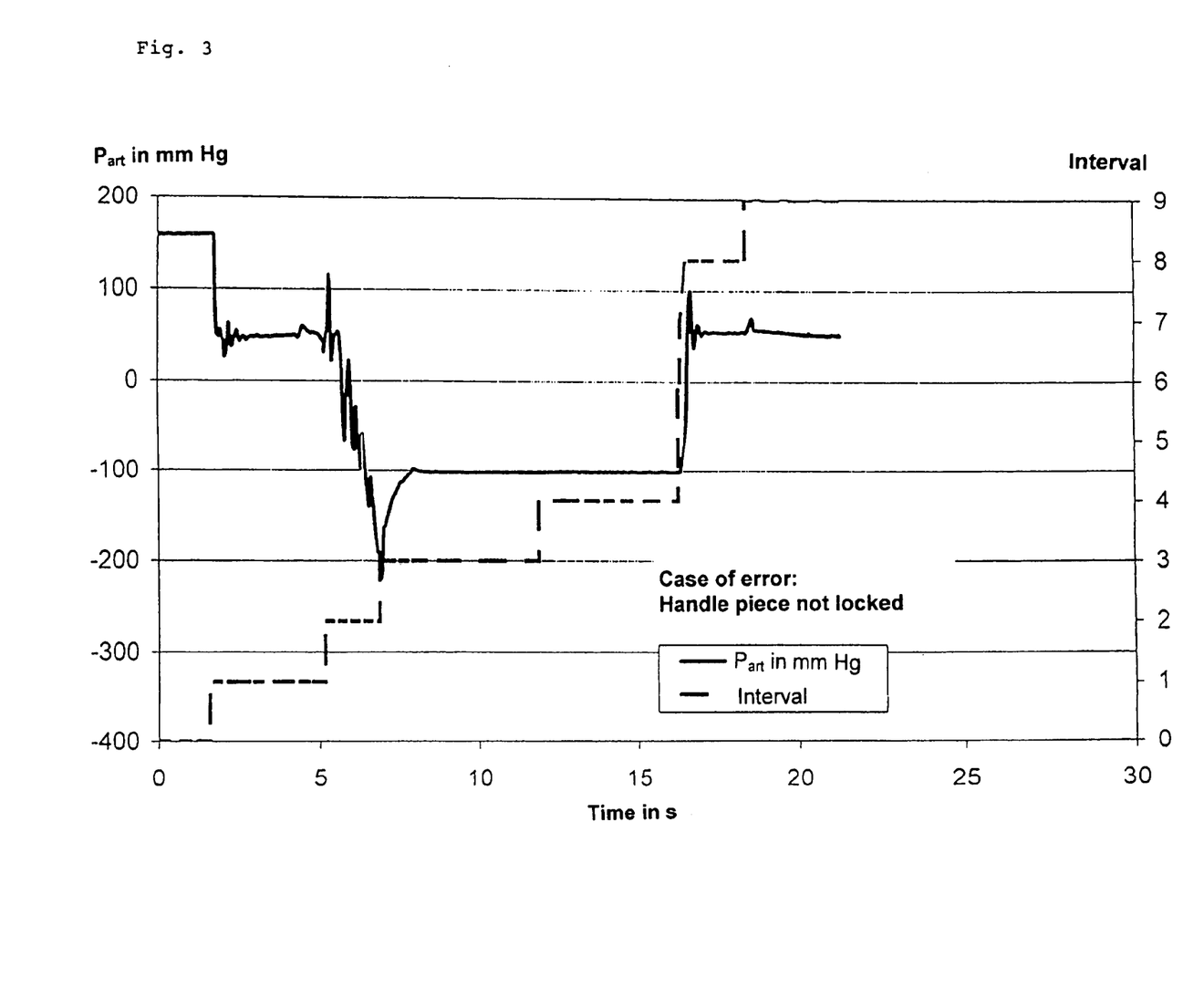
FIGS. 3-6: show pressure profile diagrams for the results of different testing procedures.

In FIG. 3, the required negative pressure cannot be built up by means of the blood pump within the volume criterion, as the angle of rotation of the blood pump is limited. Here, the case of error is shown, in which the handle piece is not locked or the heparin conduit 11 is not connected.

Figure 4:
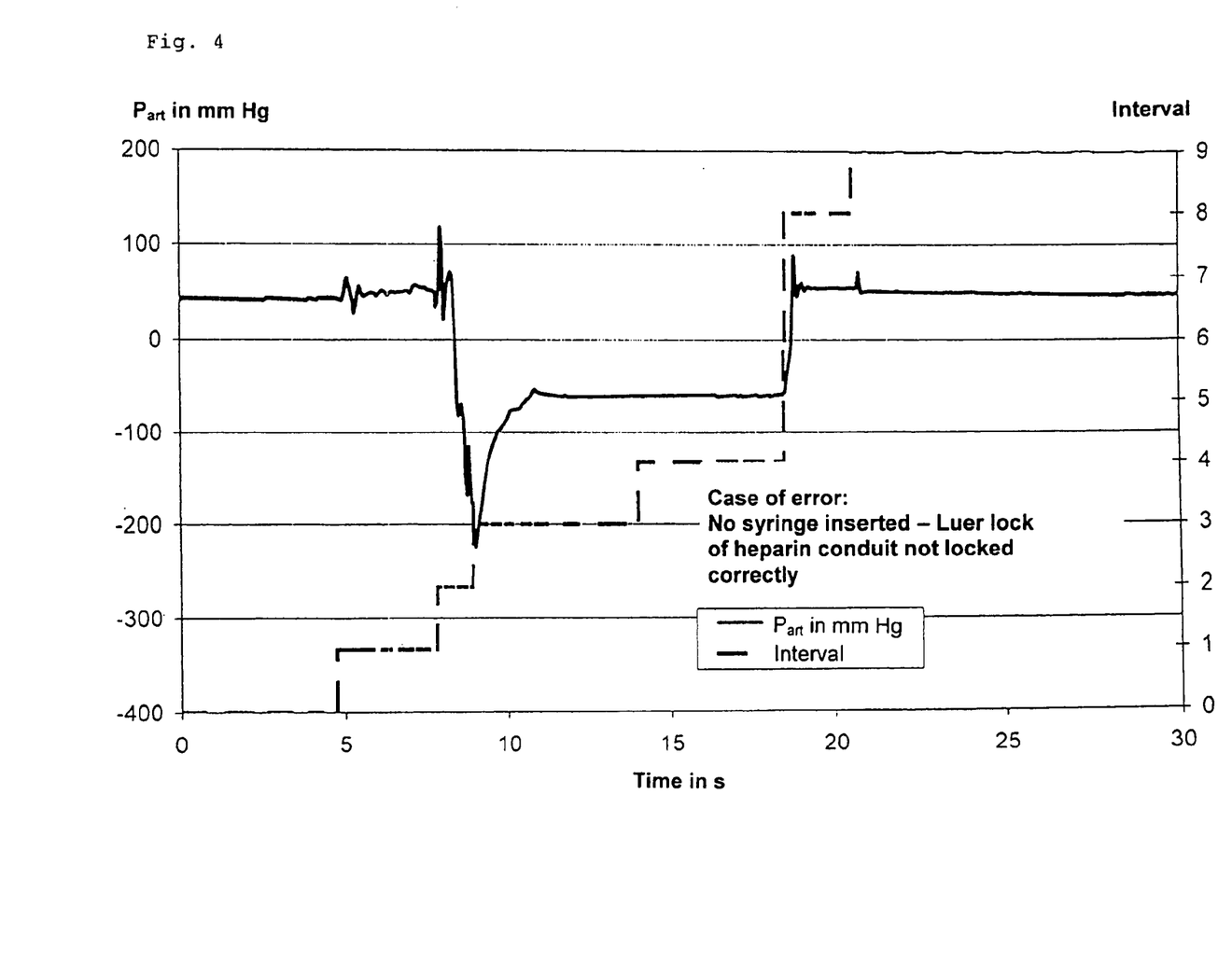

In FIG. 4, it is possible to build up the required negative pressure by means of the blood pump, i.e. the roller pump. The build-up of pressure via the heparin pump, i.e. the syringe 12, fails, however, as no fluid volume is moved. Hence it follows that either the syringe has not been inserted or the Luer lock of the heparin conduit has not been locked correctly or the heparin conduit is pinched off by means of a clamp 55.

Figure 5:
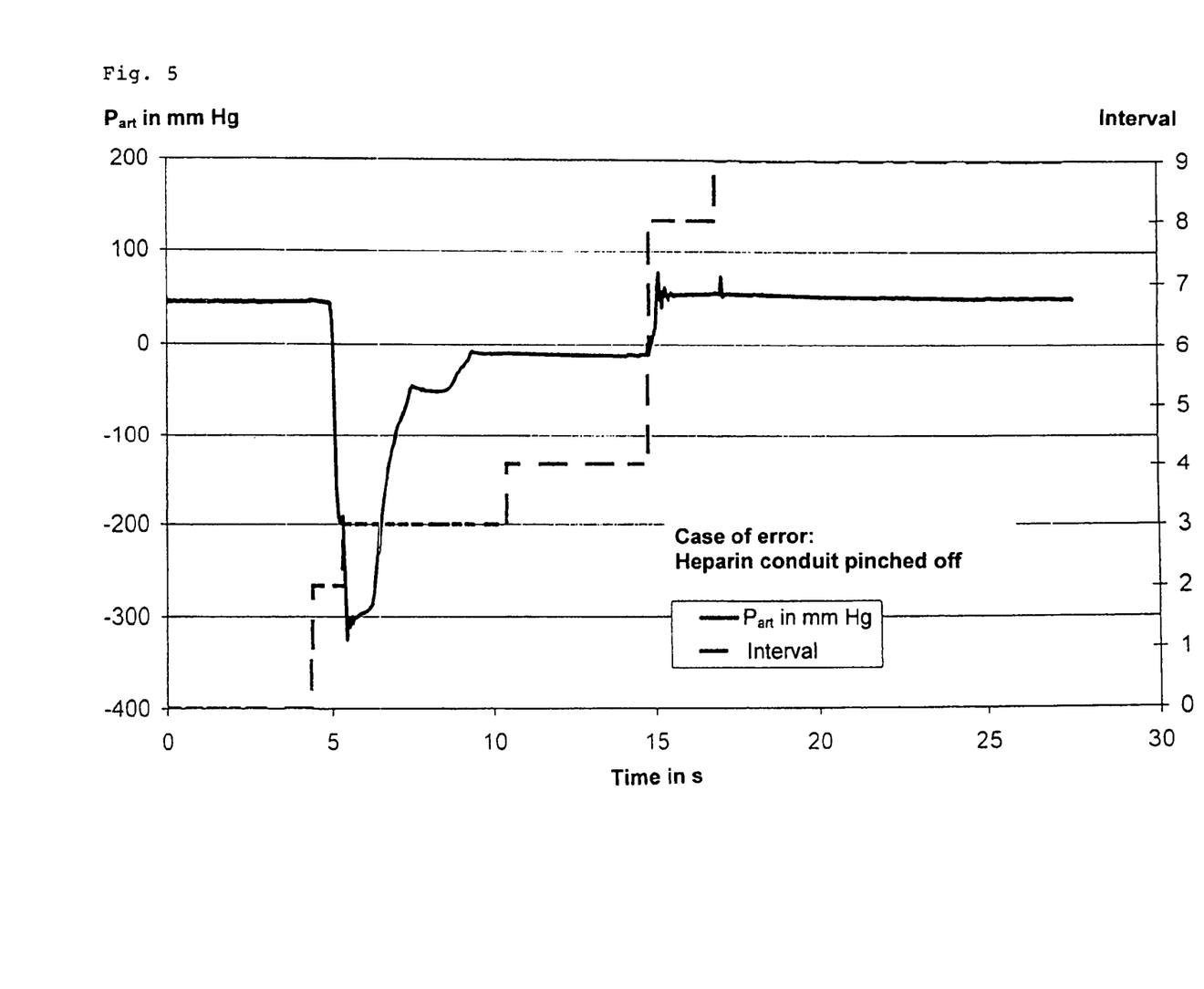

In FIG. 5, the test result reveals that the required negative pressure has been achieved by means of the blood pump 14 designed as roller pump, that the build-up of pressure via the syringe 12 is also working, but that the build-up of negative pressure by means of the syringe 12 fails, as the syringe plunger is not locked and a major negative pressure cannot be built up within the volume criterion (displacement volume of the syringe is limited).

Figure 6:
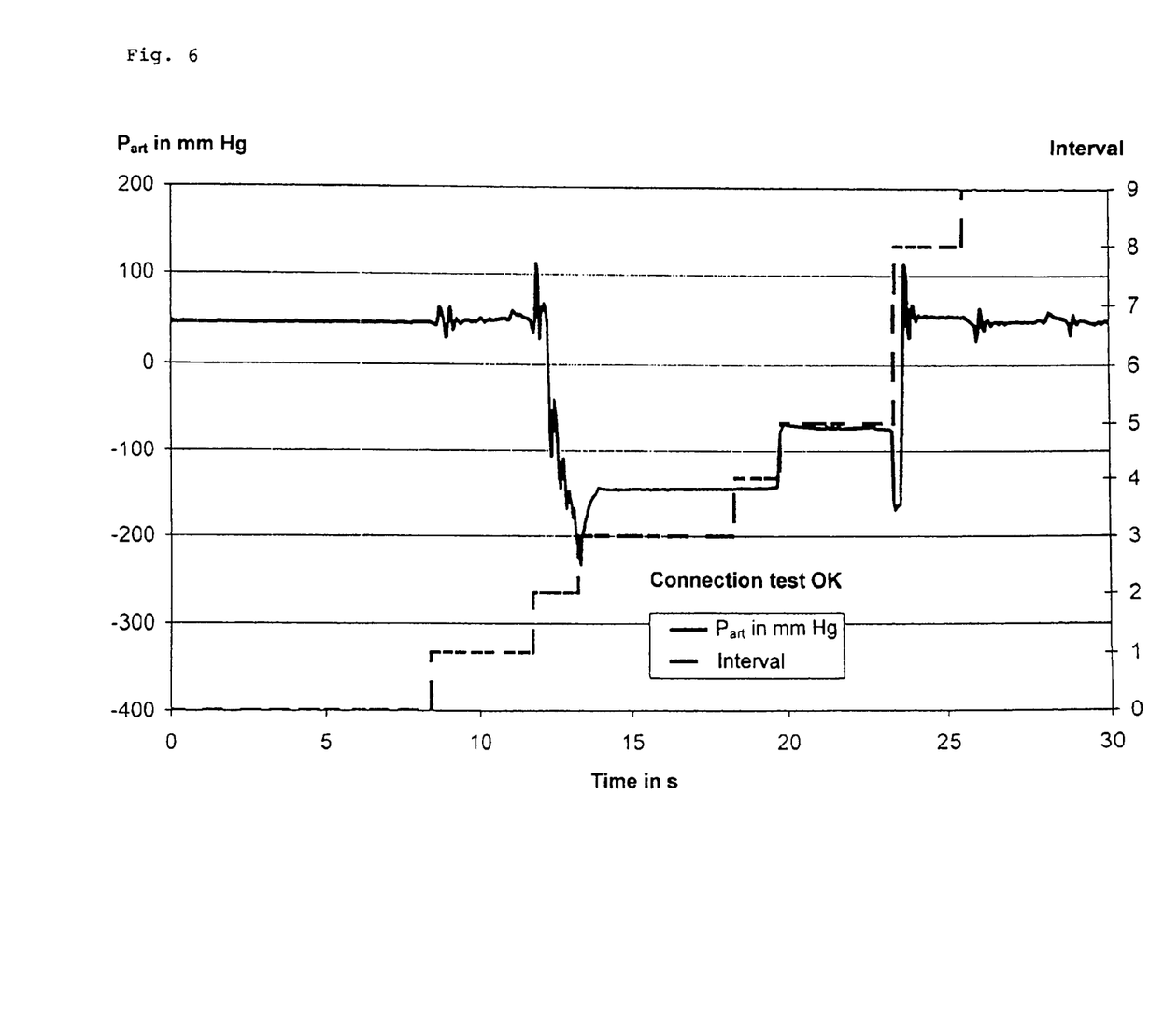

FIG. 6 finally shows the ideal condition, in which the connection test has been completed successfully. On the one hand, the required negative pressure is achieved here by means of the blood pump, and on the other hand, applying the excess pressure or the negative pressure by means of the syringe 12 is also working.

In the Figures, the stepped graphs indicated in broken lines do not reveal any measured quantities, but different intervals of the testing procedure. The intervals relate to the translation of the tests into a program. This example is a testing procedure with three basic steps, as explained above. The steps are as follows:
- the blood pump builds up a negative pressure in upstream direction;
- the heparin pump (syringe) builds up an excess pressure;
- the heparin pump (syringe) builds up a negative pressure.

This test is required, as the heparin pump (syringe 12) is arranged in the region of negative pressure of the blood pump (roller pump 14). This arrangement involves disadvantages and risks which can be minimized by the tests described above.

The risks and disadvantages are as follows:
- the plunger of the heparin pump possibly is not fixed, so that the entire heparin can be sucked in incorrectly ("unintended bolus");
- the pinch clamp in the heparin conduit possibly is not opened, so that no heparin is flowing unnoticed;
- when the heparin conduit is not tightly connected, microbubbles possibly are formed;
- a compensation of play is necessary for foreign models of the heparin pump.

The test was optimized for minimum quantities of heparin. By means of the test, the following facts are checked:
- Is the pinch clamp on the heparin conduit opened?
- Is the pinch clamp 55 on the heparin conduit correctly closed with the heparin syringe missing?
- Is the heparin syringe correctly fixed in the holder?
- Can leakages on the suction side of the blood pump be excluded?

The apparatus and the method as described above relate for instance to the set of blood tubes and the dialysis machine prior to connection of the patient.

In principle, the above-described method for checking the correct coupling can also be performed during the treatment.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of checking a correct coupling of an adding device to a therapeutic appliance that includes an extracorporeal circuit with which the adding device is coupled such that a drug can be introduced into the extracorporeal circuit with the adding device, said method comprising:
   closing a portion of the extracorporeal circuit in connection with a portion of the adding device with respect to other parts of the extracorporeal circuit, and varying and measuring a pressure in the closed portion, with the closed portion being a portion of an arterial conduit of a set of blood tubes for a method of extracorporeal blood treatment.

2. The method as claimed in claim 1, wherein a predetermined sequence of pressure conditions in a region of negative and excess pressure is applied and measured, and wherein a measured pressure profile is compared with a set-point profile.

3. The method as claimed in claim 1, wherein the adding device is a syringe pump with a syringe inserted therein.

4. The method as claimed in claim 3, wherein the drug contained in the syringe pump is an anticoagulant or another medicament.

5. The method as claimed in claim 4, wherein the anticoagulant is heparin.

6. The method as claimed in claim 1, wherein the portion of the extracorporeal circuit in connection with the portion of the adding device includes an occluding pump.

7. The method as claimed in claim 6, wherein the pump is a roller pump or a finger pump.

8. The method according to claim 6, wherein the occluding pump is a peristaltic pump.

9. The method as claimed in claim 1, wherein the pressure is measured via a pressure sensor connected with the extracorporeal circuit.

10. The method as claimed in claim 1, wherein the adding device is a syringe pump, wherein the portion of the extracorporeal circuit in connection with the portion of the adding device includes an occluding blood pump, and wherein tube portions of the arterial conduit of the set of blood tubes are subjected to different pressure conditions after closing via a clamp and via the syringe pump and the occluding blood pump.

11. The method as claimed in claim 10, wherein a torque of a motor for driving at least one of the syringe pump and the peristaltic pump is detected via a motor current and specified as a set point or set-point profile.

12. The method as claimed in claim 1, wherein the adding device is a syringe pump and the portion of the extracorporeal circuit in connection with the portion of the adding device includes a peristaltic pump, and wherein changes in the pressure are effected by specifying at least one of a translational movement of a piston of the syringe pump and an angle of rotation of the peristaltic pump, and wherein the changes in the pressure specified by the at least one of the translation and the angle of rotation are compared with a set-point profile or a set point.

13. The method as claimed in claim 12, wherein the set points or set-point profiles for the pressures are specified, and the required translational movements of the at least one of the piston of the syringe pump and the angles of rotation of the peristaltic pump are measured and compared with the specified set points or set-point profiles of the at least one of the translational movement and the angle of rotation.

14. The method as claimed in claim 1, wherein process sequences are controlled by a control device.

15. The method as claimed in claim 14, wherein the control device is integrated in the control of a blood treatment machine.

16. A therapeutic appliance configured for accommodating an extracorporeal circuit with an adding device for a drug, said appliance comprising:
  a control device that automatically checks the correct coupling of the adding device by the method according to claim 1.

17. The therapeutic appliance as claimed in claim 16, wherein the adding device is a syringe pump with a syringe inserted therein.

18. The therapeutic appliance as claimed in claim 17, wherein via a tubular conduit the syringe pump is connected to a tubular conduit of the therapeutic appliance in a region of negative pressure on a suction side of a pump.

19. The therapeutic appliance as claimed in claim 17, wherein the syringe is filled with a concentrate or a solution.

20. The therapeutic appliance as claimed in claim 16, wherein the drug is an anticoagulant or another medicament.

21. The therapeutic appliance as claimed in claim 20, wherein the anticoagulant is heparin.

22. The therapeutic appliance as claimed in claim 16, wherein the tubular conduit of the therapeutic appliance is the portion of the arterial conduit of the set of blood tubes for the method of extracorporeal blood treatment.

23. The therapeutic appliance as claimed in claim 16, wherein the method is at least one of dialysis, hemodialysis, hemofiltration, hemodiafiltration, blood purification by adsorption, transfusion, and autotransfusion.

24. The therapeutic appliance according to claim 16, wherein the appliance is a dialysis machine.

* * * * *

UNITED STATES PATENT AND TRADEMARK OFFICE
CERTIFICATE OF CORRECTION

PATENT NO.         : 8,394,046 B2                                             Page 1 of 1
APPLICATION NO. : 12/451565
DATED              : March 12, 2013
INVENTOR(S)        : Nuernberger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

First Day of September, 2015

Michelle K. Lee
*Director of the United States Patent and Trademark Office*